United States Patent [19]
Armstrong

[11] Patent Number: 5,561,138
[45] Date of Patent: Oct. 1, 1996

[54] METHOD OF TREATING ANEMIA

[75] Inventor: Jay J. Armstrong, Bensalem, Pa.

[73] Assignee: American Home Products Corporation, Madison, N.J.

[21] Appl. No.: 354,977

[22] Filed: Dec. 13, 1994

[51] Int. Cl.$^6$ .......................... A61K 31/44; A61K 35/00
[52] U.S. Cl. .......................... 514/291; 514/294; 424/122
[58] Field of Search .............................. 514/294; 424/122

[56] References Cited

U.S. PATENT DOCUMENTS

| | | | |
|---|---|---|---|
| 3,929,992 | 12/1975 | Sehgal et al. | 424/122 |
| 3,993,749 | 11/1976 | Sehgal et al. | 424/122 |
| 4,401,653 | 8/1983 | Eng | 424/122 |
| 4,885,171 | 12/1989 | Surendra et al. | 424/122 |
| 5,078,999 | 1/1992 | Warner et al. | 514/291 |
| 5,080,899 | 1/1992 | Sturm et al. | 514/291 |
| 5,100,899 | 3/1992 | Calne | 514/291 |
| 5,206,018 | 4/1993 | Sehgal et al. | 514/291 |
| 5,286,730 | 2/1994 | Caufield et al. | 514/291 |
| 5,286,731 | 2/1994 | Caufield et al. | 514/291 |
| 5,288,711 | 2/1994 | Mitchell et al. | 514/291 |
| 5,321,009 | 6/1994 | Baeder et al. | 514/291 |
| 5,387,589 | 2/1995 | Kulkarni | 514/291 |

FOREIGN PATENT DOCUMENTS

507555A1  7/1992  European Pat. Off. .
WO9202229  1/1992  WIPO ................................ 514/294

OTHER PUBLICATIONS

Andreoli, T., Essential sof Medicine, W. B. Saunders, Pub., 349–360 (1986).
Hoffbrand, A. V., Essential Hematology, Blackwell Scientific Pub. 3:37–131 (1993).
Chandrasoma, P., Concise Pathology, Appleton, and lage 1:398–400 (1991).
Venzina, C., J. Antibiot. 28:721 (1975).
Sehgal, S. N., J. Antibiot. 28:727 (1975).
Baker, H. J. Antibiot, 31:539 (1978).
Martel, R. R., Can. J. Physiol. Pharmacol. 55:48 (1977).
Staruch, M. J., FASEB 3:3411 (1989).
Dumont, F. J., FASEB 3:5256 (1989).
Calne, R. Y., Lancet 1183 (1978).
Morris, R. E., Med. Sci. Res. 17:877 (1989).
Baeder, W. L., Fifth Int. Conf. Inflamm. Res. Assoc. 121 (Abstract) (1990).
Meiser, B. M., J. Heart Lung Transplant. 11 (pt. 2):197 (1992).
Stepkowski, S. M., Transplantation Proc. 23:507 (1991).

*Primary Examiner*—Jerome D. Goldberg
*Attorney, Agent, or Firm*—Arnold S. Milowsky

[57] ABSTRACT

This invention provides a method of treating immune related anemia in a mammal which comprises administering rapamycin to said mammal orally, parenterally, intravascularly, intranasally, intrabronchially, transdermally, rectally.

4 Claims, No Drawings

METHOD OF TREATING ANEMIA

BACKGROUND OF THE INVENTION

Anemia is defined as a reduction in the hemoglobin concentration of the blood, usually associated with a reduction of total circulating red cell mass. Regardless of the cause, anemia decreases the oxygen-carrying capacity of the blood, and when severe enough, causes clinical symptoms and signs.

Clinically, anemia is characterized by pallor of the skin and mucus membranes, and by manifestations of hypoxia, most commonly weakness, fatigue, lethargy, or dizziness. Myocardial hypoxia may produce hyperdynamic circulation with an increase in heart rate and stroke volume. Ejection type flow murmurs may develop, and if the anemia is severe enough, cardiac failure may ensue.

Anemias are generally classified in one of two ways: either by etiological classification (based on the cause) or by morphologic classification (based on changes in shape and size). Etiological classification is more commonly employed. The invention covered by this application is primarily concerned with anemias implicating the immune system.

Autoimmune hemolytic anemia (AIHA) caused hemolysis occurs due to autoantibody production by the body against its own red blood cell (RBC) membrane. These anemias are divided into two classifications based on the reactivity of the antibodies involved: warm (antibody reacts at 37° C.) or cold (4° C.). [Hoffbrand, A. V. in Essential Hematology, 3rd. ed., Blackwell Scientific Publications, 1993, p. 87]. Certain immune disorders such as collagen vascular diseases, chronic inflammatory bowel disease, chronic lymphocytic leukemia, or lymphomas are associated with an increased incidence of AIHA [Andreoli, T. in Essentials of Medicine, W. B. Saunders, 1986, p. 349].

Warm AIHA is characterized by RBC coated with IgG alone, IgG with complement, or complement alone. RBCs are taken up by macrophages, especially in the spleen. Cells become more spherical to maintain volume and are prematurely destroyed, typically in the spleen, resulting in an splenomegaly and microcytosis. Warm AIHA occurs alone, or in association with other diseases, and can arise as a result of methyl dopa therapy. When it is associated with idiopathic thrombocytopenic purpura, it is known as Evan's Syndrome. Warm AIHA has an insidious onset and a chronic course. Treatments include corticosteroids (prednisolone), splenectomy, removing underlying cause (methyl dopa). Immunosuppressants may be tried after other measures fail, but are not always of great value; azathioprine, cyclophosphamide, chlorambucil, and cyclosporin A (CsA) have been tried. Blood transfusions with blood that is the least compatible and lacking antigens (if auto-Ab is known) may be needed. [Hoffbrand, A. V. in Essential Hematology; 3rd. ed., Blackwell Scientific Publications, 1993, p. 87 and Chandrasoma, P. in Concise Pathology, 1st. ed, Appleton and Lange, 1991, p. 398].

With cold AIHA, the antibody involved is usually IgM and binds to RBCs best at 4° C. The antibodies are usually directed against the 'I' antigen on the RBC, and attach to the RBCs mainly in the peripheral circulation where the blood temperature is cooled. Agglutination of RBCs by the antibody often causes peripheral circulation abnormalities. Idiopathic cold AIHA is a rare cause of hemolysis that occurs mainly in older patients. Patients may have a chronic hemolytic anemia aggravated by the cold. Patients present with cold-induced hemolysis or Raynaud's phenomenon present with mild jaundice and may develop acrocyanosis (purplish skin color) at tips of nose, ears, fingers, and toes due to the agglutination of RBC in the small vessels. Splenomegaly may be present:. Secondary cases are seen after Mycoplasma pneumonia or infectious mononucleosis. Treatment consists of keeping patient warm, and treating underlying cause, if present. Alkylating agents may be useful; splenectomy does not usually help, unless massive splenomegaly is present. Steroids are not helpful. [Hoffbrand, A. V. in Essential Hematology, 3rd. ed., Blackwell Scientific Publications, 1993, p. 89; and Chandrasoma, P. in Concise Pathology, 1st. ed, Appleton and Lange, 1991, p. 398].

Alloimmune hemolytic anemia occurs when the antibody of one individual reacts with RBC of another. Alloimmune hemolytic anemia typically occurs following transfusion of ABO incompatible blood and rhesus disease of the newborn. It also can occur following allogenic transplantation. [Hoffbrand, A. V. in Essential Hematology, 3rd. ed., Blackwell Scientific Publications, 1993, p. 90].

The administration of certain drugs can cause transient drug induced anemia. This can occur by three mechanisms: 1) antibody directed agianst a drug-red cell membrane complex (e.g., penicillin or cephalothin); 2) deposition of complement via drug-protein (antigen)-antibody complex onto the red cell surface (e.g., quinidine or chloropropamide) or 3) an autoimmune hemolytic anmeia in which the role of the drug is mysterious (e.g., methyl dopa). In each case, the anemia disappears only after the drug is discontinued (however, with methyl dopa, the antibodies may persist for many months). [Hoffbrand, A. V. in Essential Hematology, 3rd. ed., Blackwell Scientific Publications, 1993, p. 90–1].

Aplastic anemia is defined as pancytopenia (anemia, leucopenia, and thrombocytopenia) resulting from aplasia of the bone marrow. It is classified into primary types: a congenital form (Fanconi anemia) and an acquired form with no obvious precipitating cause (idiopathic). Secondary causes may result from a variety of industrial, iatrogenic and infectious causes. The underlying cause appears to be a substantial reduction in the number of hemopoietic pluripotential stem cells and a defect in the remaining stem cells or an immune reaction against them making them unable to divide and differentiate sufficiently to populate the bone marrow. [Hoffbrand, A. V. in Essential Hematology, 3rd. ed., Blackwell Scientific Publications, 1993, p. 121]. Suppresser T-cells as well as immunoglobulins that inhibit erythropopieten or block differentiation of hemopoietic stem cells in vitro have been demonstrated in some cases. [Andreoli, T. in Essentials of Medicine, W. B. Saunders, 1986, p. 349].

Fanconi type aplastic anemia is a recessively inherited condition that is associated with growth retardation and congenital defects of the skeleton, of the renal tract, skin, and often mental retardation. The typical age of presentation is 5–10 years old. Treatment; is usually with androgens or bone marrow transplantation. [Hoffbrand, A. V. in Essential Hematology, 3rd. ed., Blackwell Scientific Publications, 1993, p. 122–3].

Idiopathic acquired aplastic anemia is thought to be an autoimmune condition in which the patient's T-lymphocytes suppress the hemopoietic stem cells. Clinical response is often seen with anti-lymphocyte globulin (ALG), corticosteroids, and CsA. In some instances, a defect of the marrow stem cells which limits their proliferative capacity seems likely. [Hoffbrand, A. V. in Essential Hematology, 3rd. ed., Blackwell Scientific Publications, 1993, p. 123]. Clinical features include infections (mouth, throat, and generalized bruising, bleeding gums, epistaxes, and menorhagia. This condition is often life threatening. The lymph nodes, liver, and spleen are not enlarged. [Hoffbrand, A. V. in Essential Hematology, 3rd. ed., Blackwell Scientific Publications, 1993, p. 123–4].

ALG is of benefit in about 50–60% of acquired cases, and is thought act via the elimination of suppresser killer T-cells. Serum sickness, fever, rashes, hypotension, or hypertension, however, are side effects. CsA therapy given with ALG and high doses of corticosteroids appears to be of additional benefit. Approximately, 50–60% of patients respond to ALG and up to 80% respond to combined ALG, steroids, and CsA. CsA alone, provides improvement in an occasional patient. [Hoffbrand, A. V. in Essential Hematology, 3rd. ed., Blackwell Scientific Publications, 1993, p. 126].

Rapamycin is a macrocyclic triene antibiotic produced by *Streptomyces hygroscopicus*, which was found to have antifungal activity, particularly against *Candida albicans*, both in vitro and in vitro [C. Vezina et al., J. Antibiot. 28, 721 (1975); S. N. Sehgal et al., J. Antibiot. 28, 727 (1975); H. A. Baker et al., J. Antibiot. 31,539 (1978); U.S. Pat. No. 3,929,992; and U.S. Pat. No. 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 341 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); R. Y. Calne et al., Lancet 1183 (1978); and U.S. Pat. No. 5,100,899].

Rapamycin has also been shown to be useful in preventing or treating systemic lupus erythematosus [U.S. Pat. No. 5,078,999], pulmonary inflammation [U.S. Pat. No. 5,080,899], insulin dependent diabetes mellitus [Fifth Int. Conf. Inflamm. Res. Assoc. 121 (Abstract), (1990)], smooth muscle cell proliferation and intimal thickening following vascular injury [Morris, R. J. Heart Lung Transplant 11 (pt. 2): 197 (1992)], adult T-cell leukemia/lymphoma [European Patent Application 525,960 A1], and ocular inflammation [European Patent Application 532,862 A1].

DESCRIPTION OF THE INVENTION

This invention provides a method of treating immune related anemia in a mammal which comprises administering rapamycin to said mammal orally, parenterally, intravascularly, intranasally, intrabronchially, transdermally, rectally. Immune related anemias are defined as those anemias in which the reduction in hemoglobin concentration in the blood is at least in part attributed to either an alloimmune or autoimmune condition or disease. In particular, this invention provides a method of treating autoimmune hemolytic anemia (warm or cold), transient drug induced anemia, alloimmune anemia, and aplastic anemia through the administration of rapamycin by the above routes of administration.

Treating covers treating an existing condition, inhibiting the progress or development of the condition, ameliorating the condition, and providing palliation of the condition.

The effect of rapamycin on immune related anemias was established in an in vivo standard pharmacological test procedure that emulates the immune mediated anemias in humans. The procedure used and the results obtained are described below. Cyclosporin A was also evaluated in the standard pharmacological test procedure for comparison.

W/W$^v$ mice, a congenitally anemic strain were divided into two treatment groups and two control groups. One treatment group received rapamycin (12 mg/kg daily) intraperitoneally for thirty days. The second treatment group received cyclosporin A (60 mg/kg daily) intraperitoneally for thirty days. The first control group received a daily intraperitoneal injection of vehicle (8% cremophor EL, 2% ethanol, and 90% water) for thirty days, and the second control group received no treatment. Additionally, W/W$^+$ non-anemic mice received rapamycin, vehicle, or no treatment according to the above regimens. Blood parameter evaluation (RBC count, hemoglobin concentration, and hematocrit) was determined on a weekly basis for fifty days.

The results obtained are shown in the tables below. Table 1 shows the percent change from baseline in the red blood cell count; Table 2 shows the percent change from baseline in hemoglobin levels; and Table 3 shows the percent change from baseline in hematocrit values.

TABLE 1

RBC PERCENT CHANGE FROM BASELINE (MEAN ± S.E.)

| Day | Anemic/RAP* | Anemic/CsA | Anemic/Veh | Anemic/NT[+] | Non-Anemic/RAP | Non-Anemic/Veh | Non-Anemic/NT[+] |
|---|---|---|---|---|---|---|---|
| 7 | −4.55 ± 3.10 | −2.04 ± 3.60 | −4.24 ± 1.48 | −2.25 | 3.20 ± 1.88 | −0.41 ± 2.04 | 1.71 |
| 14 | 20.00 ± 2.26 | 12.12 ± 4.54 | 2.89 ± 2.15 | 1.50 | −0.62 ± 1.86 | −5.67 ± 1.28 | −1.61 |
| 21 | 25.76 ± 5.94 | 13.17 ± 3.07 | −5.15 ± 2.84 | −0.60 | 1.78 ± 1.04 | −9.33 ± 2.18 | −1.11 |
| 28 | 14.97 ± 2.26 | −1.76 ± 2.48 | −3.48 ± 2.75 | 4.50 | −6.55 ± 0.90 | −11.96 ± 1.52 | −9.26 |
| 35/36 | 20.39 ± 3.10 | 1.84 ± 4.68 | −6.36 ± 3.44 | −1.65 | −6.71 ± 1.26 | −15.98 ± 1.39 | −14.50 |
| 42 | 9.76 ± 2.69 | −1.73 ± 3.90 | −12.16 ± 4.19 | 0.75 | −10.69 ± 1.46 | −7.50 ± 1.34 | −7.65 |
| 49/53 | 14.35 ± 4.68 | 3.68 ± 3.94 | −1.49 ± 2.51 | −1.20 | −16.04 ± 3.06 | −15.71 ± 2.70 | −12.99 |

*RAP = rapamycin; CsA = cyclosporin A; Veh = vehicle; NT = no treatment; Anemic = anemic mice; Non-Anemic = non-anemic mice.
[+]Standard error was not calculated for the no treatment groups.

TABLE 2

HEMOGLOBIN PERCENT CHANGE FROM BASELINE (MEAN ± S.E.)

| Day | Anemic/RAP* | Anemic/CsA | Anemic/Veh | Anemic/NT[+] | Non-Anemic/RAP | Non-Anemic/Veh | Non-Anemic/NT[+] |
|---|---|---|---|---|---|---|---|
| 7 | −2.95 ± 3.83 | −7.71 ± 2.80 | −6.34 ± 1.29 | −5.57 | 4.40 ± 2.24 | 1.09 ± 1.19 | −3.20 |
| 14 | 14.50 ± 1.88 | −0.30 ± 3.96 | −0.81 ± 1.85 | 0.43 | −1.03 ± 1.79 | −6.85 ± 0.78 | −3.20 |
| 21 | 22.32 ± 5.90 | −0.94 ± 2.70 | −8.65 ± 2.17 | 0.21 | 0.38 ± 1.19 | −9.91 ± 1.91 | −3.20 |
| 28 | 10.87 ± 1.61 | −11.63 ± 2.53 | −5.20 ± 2.52 | 4.28 | −5.84 ± 1.53 | −12.47 ± 1.28 | −11.55 |
| 35/36 | 9.41 ± 2.26 | −4.42 ± 6.33 | 0.03 ± 1.67 | 6.21 | −2.28 ± 1.40 | −16.17 ± 1.02 | −14.21 |
| 42 | 5.98 ± 2.54 | −7.50 ± 3.80 | −0.92 ± 3.19 | 4.07 | −10.99 ± 1.57 | −6.07 ± 1.49 | −6.75 |
| 49/53 | 7.58 ± 3.20 | −7.85 ± 2.94 | −7.25 ± 3.37 | 4.71 | −14.09 ± 2.31 | −13.41 ± 1.94 | −3.73 |

*RAP = rapamycin; CsA = cyclosporin A; Veh = vehicle; NT = No Treatment; Anemic = anemic mice; Non-Anemic = non-anemic mice.
[+]Standard error was not calculated for the no treatment groups.

TABLE 3

HEMATOCRIT PERCENT CHANGE FROM BASELINE (MEAN ± S.E.)

| Day | Anemic/RAP* | Anemic/CsA | Anemic/Veh | Anemic/NT[+] | Non-Anemic/RAP | Non-Anemic/Veh | Non-Anemic/NT[+] |
|---|---|---|---|---|---|---|---|
| 7 | −8.62 ± 3.08 | −10.92 ± 3.09 | −8.88 ± 1.53 | −8.00 | 4.18 ± 1.92 | −3.25 ± 1.46 | −2.38 |
| 14 | 15.81 ± 1.67 | −1.96 ± 3.75 | −0.30 ± 1.46 | −0.59 | −1.08 ± 2.03 | −1.58 ± 1.48 | −7.14 |
| 21 | 23.16 ± 6.09 | −1.59 ± 2.35 | −6.85 ± 1.96 | −2.08 | 4.16 ± 1.33 | −7.02 ± 1.92 | −6.55 |
| 28 | 10.46 ± 1.57 | −14.50 ± 2.31 | −5.63 ± 2.21 | 3.12 | −7.13 ± 0.82 | −12.65 ± 1.36 | −10.12 |
| 35/36 | 19.22 ± 2.36 | −2.06 ± 4.83 | −5.46 ± 3.32 | −8.01 | −3.88 ± 1.40 | −12.54 ± 1.14 | −13.10 |
| 42 | 5.62 ± 2.52 | −4.63 ± 3.44 | −9.55 ± 4.07 | −5.04 | −9.16 ± 1.93 | −5.19 ± 1.20 | −4.76 |
| 49/53 | 13.40 ± 4.29 | 5.19 ± 3.97 | 0.35 ± 2.48 | −5.79 | −4.18 ± 3.31 | −6.84 ± 2.20 | −15.48 |

*RAP = rapamycin; CsA = cyclosporin A; Veh = vehicle; NT = no treatment; Anemic = anemic mice; Non-Anemic = non-anemic mice.
[+]Standard error was not calculated for the no treatment groups.

The results of this standard test procedure demonstrate that rapamycin is useful in treating immune related anemia. The red blood cell count, hemoglobin levels, and hematocrit values did not decrease from baseline. As expected, the blood parameters decreased from baseline in the anemic vehicle treated mice. The blood parameters for the rapamycin treated mice actually improved versus baseline, indicating that rapamycin successfully inhibited anemic conditions in congenitally anemic mice. Moreover, the inhibition of anemia was observed after treatment with rapamycin had ceased, as the mice were only treated for 30 days. The results also showed that cyclosporin A did not inhibit the development of anemia in the group treated with cyclosporin A.

Based on these results, rapamycin is particularly useful in treating autoimmune hemolytic anemia (warm or cold), transient drug induced anemia, alloimmune anemia, and aplastic anemia.

Rapamycin can be formulated neat or with a pharmaceutical carrier to a mammal in need thereof. The pharmaceutical carrier may be solid or liquid. When formulated orally, it has been found that 0.01% Tween 80 in PHOSAL PG-50 (phospholipid concentrate with 1,2-propylene glycol, A. Nattermann & Cie. GmbH) provides an acceptable oral formulation.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, lethicins, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. Rapamycin can also be administered orally either in liquid or solid composition form.

Rapamycin may be administered rectally in the form of a conventional suppository. For administration by intranasal or intrabronchial inhalation or insufflation, rapamycin may be formulated into an aqueous or partially aqueous solution, which can then be utilized in the form of an aerosol. Rapamycin may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermiable membrane covering a reservoir containing the active ingredient with or without a carrier, or a matrix containing the active ingredient. Other occlusive devices are known in the literature.

In addition, rapamycin may be employed as a solution, cream, or lotion by formulation with pharmaceutically acceptable vehicles containing 0.1–5 percent, preferably 2%, of active compound which may be administered to a fungally affected area.

The dosage requirements vary with the particular compositions employed, the route of administration, the severity of the symptoms presented and the particular subject being treated. Based on the results obtained in the standard pharmacological test procedures, projected intravenous daily dosages of active compound would be 0.1 µg/kg–100 mg/kg, preferably between 0.001–25 mg/kg, and more preferably between 0.01–5 mg/kg. Projected daily oral dosages of rapamycin would be 0.005–50 mg/kg, preferably between 0.01–25 mg/kg, and more preferably between 0.05–10 mg/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is subdivided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

What is claimed is:

1. A method of treating immune related anemia in a mammal consisting essentially of administering rapamycin to said mammal orally, parenterally, intravascularly, intranasally, intrabronchially, transdermally, rectally.

2. The method according to claim 1 wherein route of administration is oral or parenteral.

3. A method of treating warm or cold autoimmune hemolytic anemia, transient drug induced anemia, alloimmune anemia, or aplastic anemia in a mammal consisting essentially of administering rapamycin to said mammal orally, parenterally, intravascularly, intranasally, intrabronchially, transdermally, rectally.

4. The method according to claim 3 wherein route of administration is oral or parenteral.

* * * * *